United States Patent
Hebert

(12)
(10) Patent No.: US 6,387,067 B1
(45) Date of Patent: May 14, 2002

(54) SHOULDER SUPPORT DEVICE FOR CORRECT SHOULDER POSTURE

(76) Inventor: Jeanne E. Hebert, 187 Deerfield Rd., Candia, NH (US) 03034

( * ) Notice: Subject to any disclaimer, the term of this patent is extended or adjusted under 35 U.S.C. 154(b) by 0 days.

(21) Appl. No.: 09/464,627

(22) Filed: Dec. 17, 1999

(51) Int. Cl.[7] .............................. A61F 13/00; A61F 5/02
(52) U.S. Cl. ..................................... 602/20; 2/44; 2/45
(58) Field of Search ............................ 2/44, 45; 602/4, 602/20, 19

(56) References Cited

U.S. PATENT DOCUMENTS

| | | | | |
|---|---|---|---|---|
| 245,524 A | * | 8/1881 | Lubin | 2/41 |
| 1,587,716 A | * | 6/1926 | Fritsch | |
| 2,723,664 A | * | 11/1955 | Davis | 128/78 |
| 5,954,681 A | * | 9/1999 | Brooks | 602/75 |

OTHER PUBLICATIONS

Dr. Leonard's, America's Leading Discount Healthcare Catalog, Page's 9, "Posture S'Port", 13 "Back Support", 22 "Perfect Posture Back Support" and "Improve Posture Support & Look Slimmer Instantly" and 34 "Magnetic Posture Support".

* cited by examiner

Primary Examiner—Kim M. Lewis
(74) Attorney, Agent, or Firm—Davis & Bujold, P.L.L.C.

(57) ABSTRACT

A shoulder support device for facilitating correct posture of the shoulders of a wearer of the device. The shoulder support device comprising an elongate base member having first and second opposed free ends. Each of the first and second opposed free ends having a mating attachment component to facilitate releasable coupling of the first and second opposed free ends with one another. A spine support area is provided along an intermediate portion the elongate base member. A first end of a pair of spaced apart shoulder strap members is secured to the elongate base member, adjacent the spine support area, and the second end of each of the shoulder strap members is secured to the elongate base member spaced from the spine support area such that the second ends of each of the shoulder strap members are located in communication with an arm pit of the wearer. The pair of spaced apart shoulder strap members each exert, during use, a rearward and downward resulting force on each respective shoulder of the wearer to influence both of the shoulders of a wearer into a correct posture position.

20 Claims, 4 Drawing Sheets

SHOULDER SUPPORT DEVICE FOR CORRECT SHOULDER POSTURE

The present invention relates to a support device to be worn by an individual to maintain the shoulders of the individual in a correct posture position, especially when the individual is performing repetitive motions for a long period of time.

BACKGROUND OF THE INVENTION

There are a variety of known support devices and apparatuses, which are currently available in the market place, that facilitate maintaining the neck, the back, the upper back, the spine, etc. in a correct position. However, many of these devices are somewhat cumbersome to utilize and do not function properly to maintain the shoulders of an individual in the correct posture—they do not exert both a rearward and a downward force on the shoulders to induce correct posture. Moreover, many of these currently available devices and apparatuses are fairly difficult to utilize and are relatively expensive to manufacture.

SUMMARY OF THE INVENTION

Wherefore, it is an object of the present invention to overcome the above noted drawbacks associated with the prior art support devices and apparatuses.

Another object of the present invention is to provide a flexible, lightweight shoulder support device that facilitates positioning the shoulders of an individual in the correct posture position, to minimize any pain and discomfort experienced by a wearer, especially when the wearer is performing repetitive motion for a long period of time.

A further object of the present invention is to provide a relatively inexpensive shoulder support device which can be easily worn, in an undetected manner, underneath ordinary clothing of the wearer.

Yet another object of the invention is to provide a shoulder support device which simultaneously applies both a suitable rearward and downward pressure or force, on each shoulder of the wearer, to bias both shoulders of the wearer of the device into the correct posture position and minimize any pain and/or discomfort experienced by the wearer during use of the shoulder support device.

A still further object of the invention is to provide a shoulder support device which does not have any shoulder strap members overlying or overlapping the spine of the wearer of the device, i.e. only the single layer base member overlaps the spine, to minimize any discomfort and/or pain experienced by the wearer of the shoulder support device in the spinal area.

Another object of the invention is to provide a shoulder support device which prevents, or minimizes at the very least, an individual from slouching when working at a desk, a computer, etc. for an extend period of time.

A still further object of the invention is to allow an individual to retain or maintain his or her muscle tone due to the continued ability of the individual to work, play, exercise, etc. and thus continue to move over a wide range of motions.

The present invention relates to a shoulder support device for facilitating correct posture of shoulders of a wearer, the shoulder support device comprising: an elongate base member having first and second opposed free ends, each of the first and second opposed free ends having a mating attachment component to facilitate releasable attachment of the first and second opposed free ends with one another, and a spine support area being provided along an intermediate portion of the elongate base member for overlying a spine of the wearer; a pair of spaced apart shoulder strap members each having first and second opposed ends, the first end of each shoulder strap member being secured to the elongate base member adjacent the spine support area, and the second end of each of the shoulder strap member being secured to an intermediate portion of the elongate base member such that the second end of each of the shoulder strap member is located to communicate with an arm pit of the wearer, during use, whereby each of the pair of spaced apart shoulder strap members exerts a resulting rearward and downward basing force on each shoulder of the wearer to influence each shoulder of the wearer into a correct posture position.

The above and other objects of the present invention will be further understood with reference to the following description and accompanying drawings as well as the appended claims.

BRIEF DESCRIPTION OF THE DRAWINGS

The invention will now be described, by way of example, with reference to the accompanying drawings in which.

DETAILED DESCRIPTION OF THE INVENTION

Figure 1:
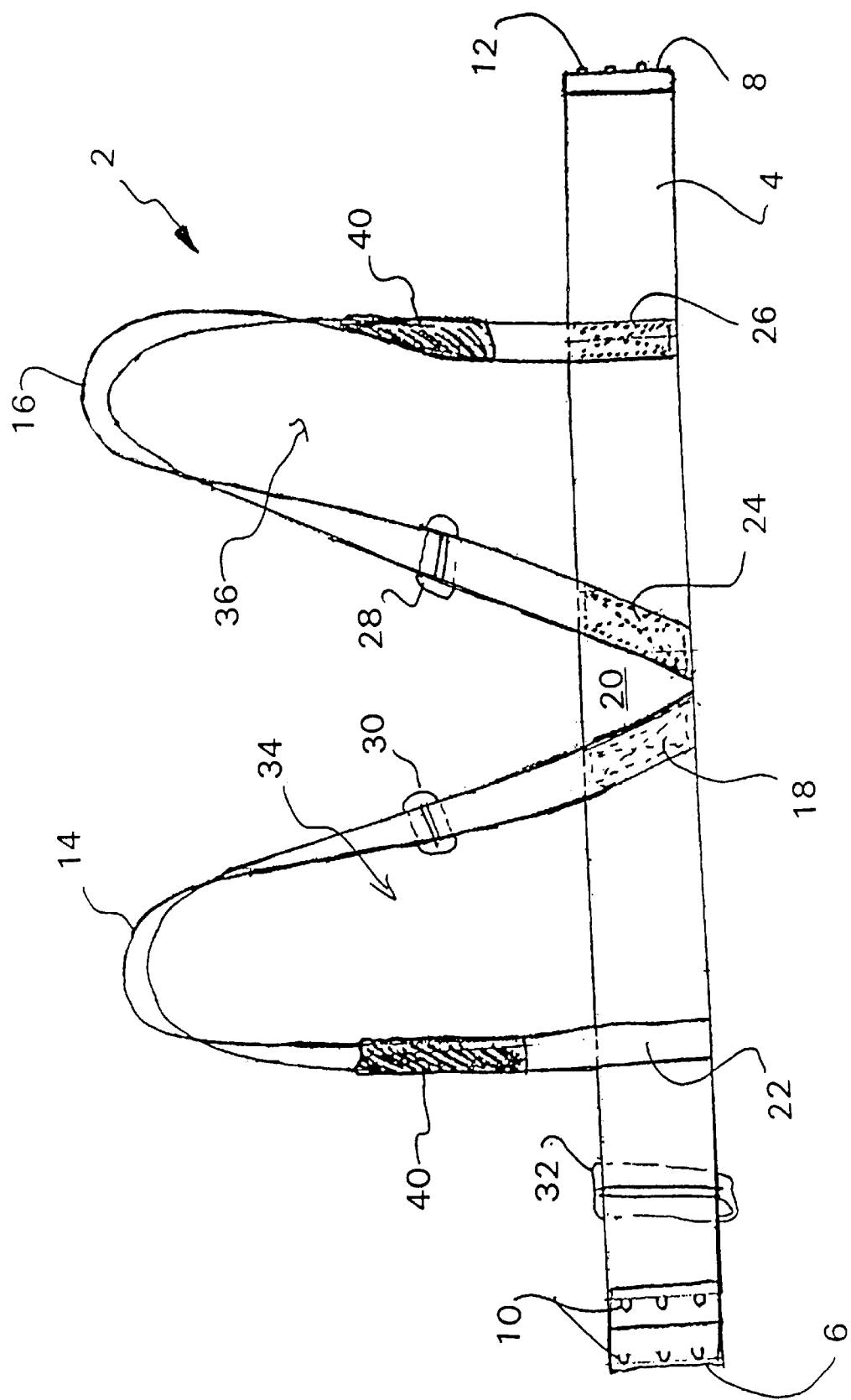
FIG. 1 is a diagrammatic top plan view showing the shoulder support device, according to the present invention, in an unfolded condition.
Figure 2:
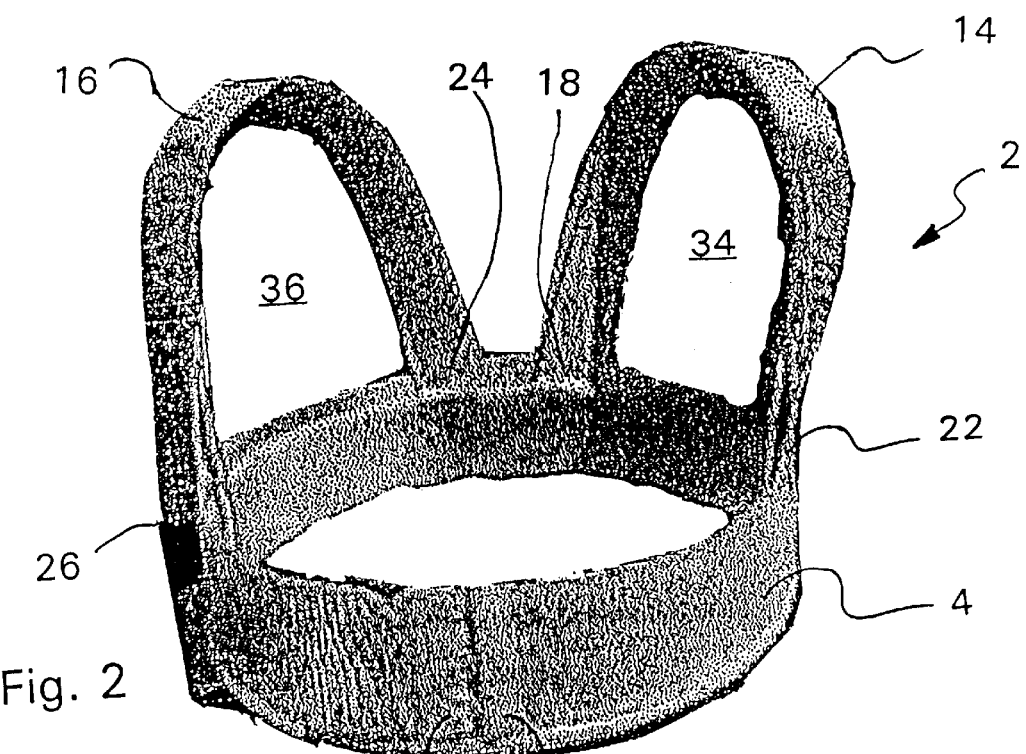
FIG. 2 is a perspective front elevational view of the shoulder support device of FIG. 1 shown in a connected state.
Figure 3:
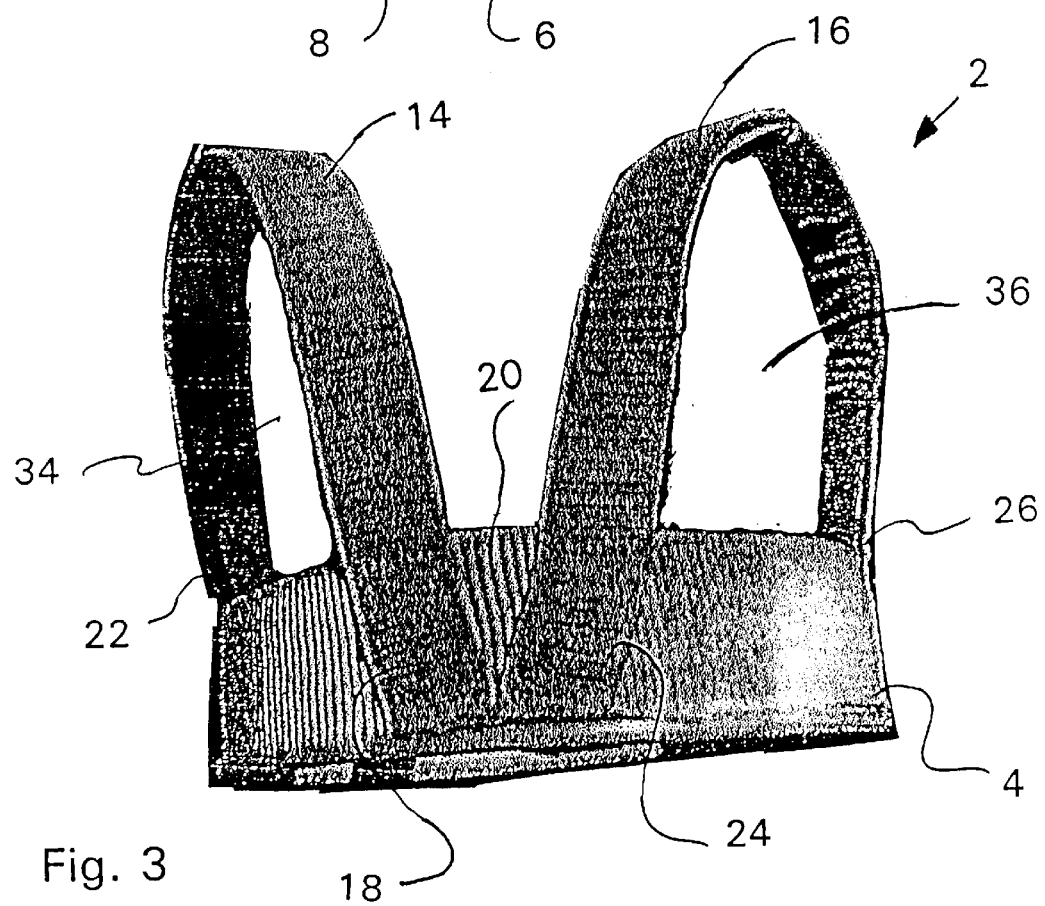
FIG. 3 is a perspective rear elevational view of the shoulder support device of FIG. 2.

Turning first to FIGS. 1–3, a detailed description concerning the present invention will first be provided. This description will then be followed by detailed explanation concerning use of the present invention.

As can be seen in those Figures, the shoulder support device 2 generally comprises an elongate, flexible, continuous width resilient base member 4 which is sized to fit snugly about the circumference of a chest portion, e.g. a central or an upper chest portion, of a wearer. The resilient base member 4 has a length typically between 24 and 50 inches, more preferably between 30 and 38 inches; a width typically between ½ to 4 inches, more preferably a width of between about 1½ inches and 3½ inches; and a thickness of typically between 1/16 to about ⅛ inches. The base member 4 is typically manufactured from a conventional ribbed elastic material as well as other conventional resilient materials.

First and second opposed free ends 6, 8 of the base member 4 are each provided with one releasably mating attachment component 10 or 12, such as hook and loop touch fasteners, conventional snaps, conventional wire hooks and loops, etc. It is to be appreciated that a variety of other conventional and well known engagable fasteners can be employed for releasably engaging and disengaging, as desired, the opposed free ends 6, 8 of the base member 4 with one another. As such fasteners are well known, a further detailed description concerning the same is not provided. If desired, a plurality of adjacent spaced apart rows of one of the attachment components 10 can be provided along at least one free end 6 of the base member 4 to facilitate adjustment of the engaged circumference of the base member 4.

A pair of spaced apart shoulder strap members 14, 16 are secured to the base member 4. A first end 18 of a first shoulder strap member 14 is attached by stitching adjacent but spaced slightly, e.g. 1/10–1 inch or so, from a spine support area 20 of the shoulder support device 2 while a second opposed end 22 of the first shoulder strap member 14 is secured by stitching to an intermediate portion of the base member 4, e.g. is secured at a located between the spine support area 20 and the free end 6 of the base member 4.

A first end 24 of the second shoulder strap member 16 is attached by stitching adjacent but on the other side of and spaced slightly, e.g. 1/10–1 inch or so, from the spine support area 20 of the shoulder support device 2 while a second opposed end 26 of the second shoulder strap member 16 is secured by stitching to an intermediate portion of the base member 4, e.g. at a located between the spine support area 20 and the free end 8 of the base member 4. If desired, the second opposed ends 22, 26 of the first and second shoulder strap members 14, 16 can be releasably attached to the base member 4, e.g. by mating touch fasteners components or the like, to facilitate adjustment of the exact location where the second opposed ends 22, 26 of the first and second shoulder strap members 14 and 16 are secured to the base member 4, and such adjustment feature is discussed below in further detail with reference to FIG. 6.

The first and second shoulder strap members 14, 16 each typically have a length of between 16 and 32 inches, more preferably a length of between 20 and 26 inches; typically have a width of between ½ inches to 2.5 inches, more preferably a width of between about 1¼ inches and 1½ inches; and a thickness of typically between 1/16 to about 1/8 inches. The first and second strap members 14, 16 each are typically manufactured from a conventional ribbed elastic material as well as other conventional resilient materials.

In addition, each one of the first and second shoulder strap members 14, 16 has a desired length to fit over one of the shoulders of the wearer of the device 2 to provide proper support to the respective shoulders. It is to be appreciated, however, that both the length of the base member 4 as well as the length of each of the shoulder strap members 14, 16 can be adjustable by a respective movable coupling 28, 30, 32 only diagrammatically shown in FIG. 1, or a releasable overlapped engagement 28', 30', 32' (e.g. by use of mating touch fasteners carried by abutting surfaces as diagrammatically shown in FIG. 6) to facilitate minor adjustments in the length of either or both the base member 4 and/or the first arid second shoulder strap members 14, 16, by the wearer, to ensure proper shoulder positioning and comfort. As such adjustment feature is conventional and well known in the art, a further detailed description concerning the same is not provided.

The spine support area 20 is preferably either generally triangular in shape (FIG. 1) or generally trapezoidal in shape (FIG. 6) to provide a suitably sized area which overlaps or lies over the spine of a wearer but does not locate any portion of the shoulder strap members in this area. The spine support area 20 is part of the base member 4 and is delimited by the first ends 18, 24 of the first and second shoulder strap members 14, 16. The primary function of the spine support area 20 is to space the first and second shoulder strap members 14, 16 from the spine of the wearer to prevent the shoulder strap members 14, 16 from pulling or rubbing against the spinal column. To maximize comfort, it is important that neither the first nor the second shoulder strap members 14, 16 extends or crosses over the soft tissue of the trapezius muscle. In the event that the first ends 18, 24 of either of the shoulder strap members 14, 16 extends or crosses over the trapezius muscle, this can result in soreness, pressure, and/or fatigue to the wearer of the device 2.

Figure 4:
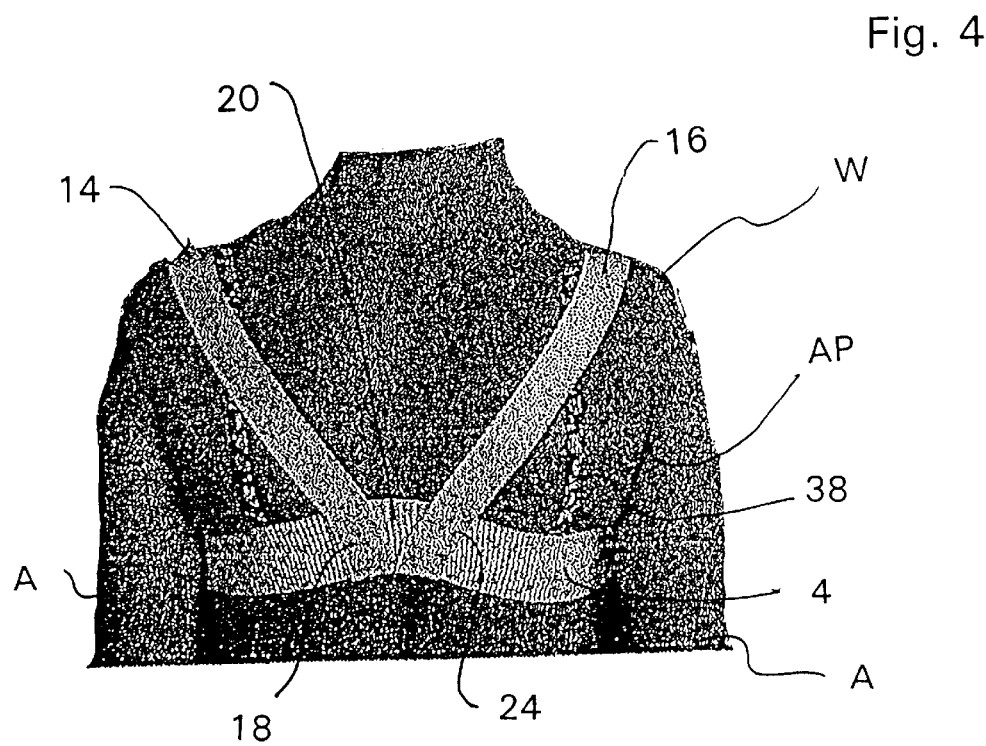
FIG. 4 is a rear side elevational view of the shoulder support device of FIG. 2 shown worn by a wearer.

With references to FIG. 4 or 5, use of the shoulder support device 2 of the present invention will now be described. When a wearer W decides to utilize the shoulder support device 2, according to the present invention, the wearer will first ensure that the mating attachment components 10, 12 are disengaged from one another. Thereafter, the wearer W will pass his or her left arm between an opening 34 formed between the first shoulder strap member 14 and the base member 4 and likewise will pass his or her right arm through the opening 36 formed between the second shoulder strap member 16 and the base member 4. The wearer W will then adjust the shoulder support device 2 to ensure that the spine support area 20 over lies the spine of the wearer W. Once this has occurred, the wearer W then engages the attachment components 10, 12 with one another so that the base member 4 extends completely around the chest portion of the wearer, but below a bra 38 if a female wearer W is wearing the shoulder support device 2. It is to be appreciated that the base member 4 must snugly fit around the circumference of the chest portion of the wearer W to anchor the shoulder support device 2 at a desired position. If necessary, the length of the base member 4 can be adjusted, via the movable coupling 32 or the overlapped engagement 32' as noted above, to facilitate the desired snug fitting engagement of the base member 4 about the chest portion.

According to one form of the invention, the length of the base member 4 is customize, i.e. manufactured to a desired pre-measured length, to snugly wrap around the chest of the wearer W without the need for any length adjustment.

Figure 5:
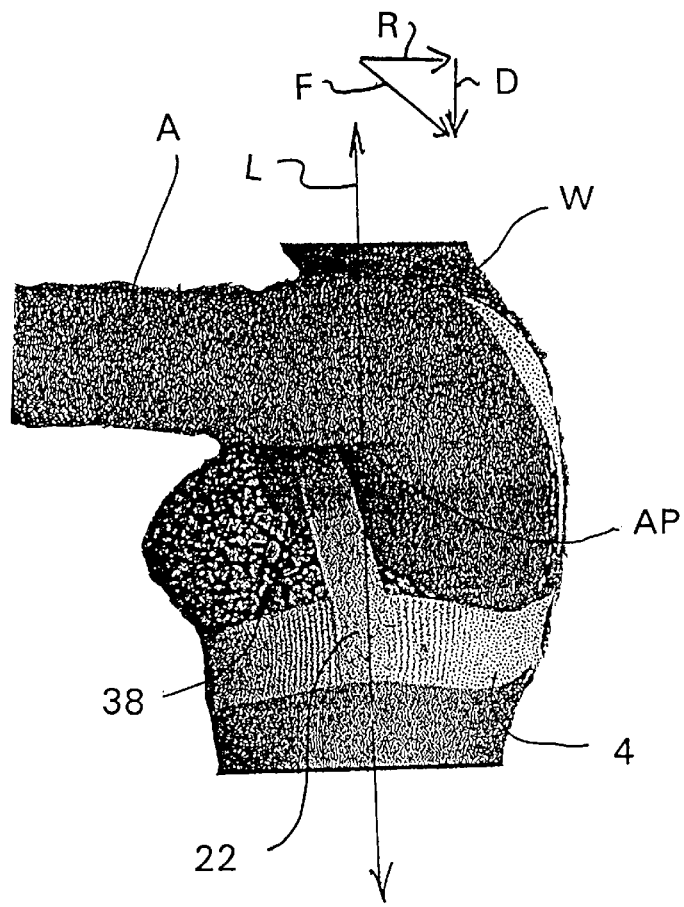
FIG. 5 is a left side elevational view of the shoulder support device of FIG. 4.

In the event that the shoulder support device 2 is correctly positioned, at least a portion of a rearward most portion of each of the second opposed ends 22, 26 of the first and second shoulder strap members 14, 16 will be located slightly rearward of the wearer W, i.e. slightly rearward (to the right as seen in FIG. 5) of an imaginary centerline L extending through the wearer W, so that when the arm A of the wearer W is hanging substantially vertically down and the wearer W is standing up, at least a portion of the second opposed ends 22, 26 will be at least partially accommodated by an armpit AP of the wearer W. As the second opposed ends 22, 26 are located slightly rearward of a forward most portion of the shoulder of the wearer W, the first and second shoulder strap members 14, 16 will each exert a rearward biasing force on the respective shoulder biasing that respective shoulder in a rearward direction, indicated by arrow R. In addition, as the shoulder strap members 14, 16 are also under slight tension, two shoulder strap members 14, 16 will each exert a downward biasing force on the respective shoulder pushing that respective shoulder in a downward direction, indicated by arrow D. The combination of these two exerted forces is a resulting force indicated by arrow F. This resulting force F facilitates biasing each respective shoulder into a correct position to maintain the shoulders of the wearer W in a correct posture and prevent slouching, even when the wearer is doing repetitive work for an extended period of time.

To maximize comfort of the shoulder support device 2, each one of the shoulder strap members 14, 16 is provided with either a fixed or an adjustable padded member 40 (FIG. 1). The two adjustable padded members 40 each facilitate spreading or dissipating some of the resulting force F, induced on the respective shoulders, to allow the shoulder support device 2 to be worn for prolonged periods of time without fatigue or discomfort to the wearer W.

Figure 6:
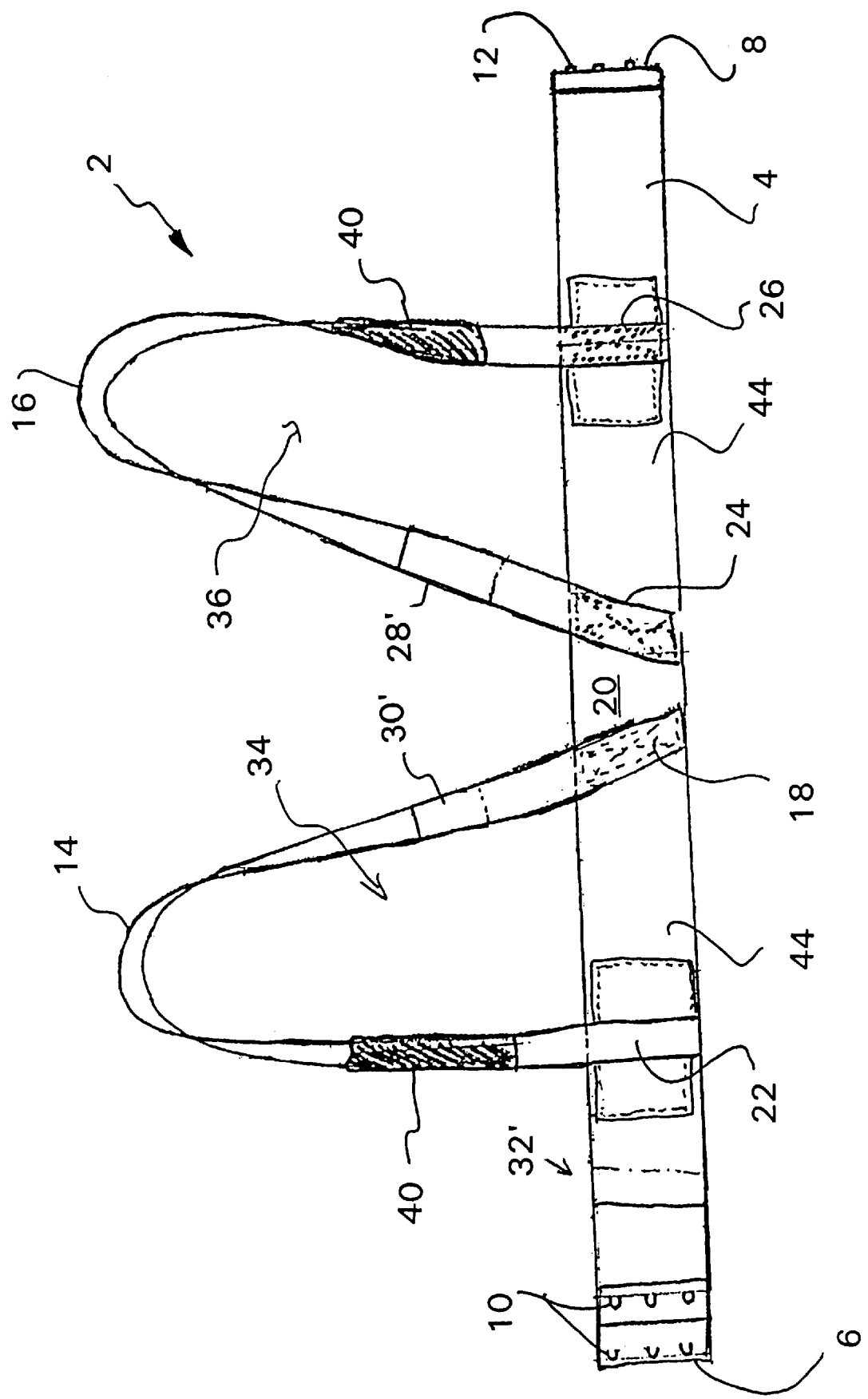
FIG. 6 is a diagrammatic top plan view showing a second embodiment of the shoulder support device, according to the present invention, in an unfolded condition.

With reference to FIG. 6, the second embodiment of the invention will now be described. As this embodiment is very similar to the first embodiment, only the differences between the first embodiment and the second embodiment will be discussed in detail.

As can be seen in FIG. 6, the only variation between the second embodiment and the first embodiment is that the location where the second opposed ends 22 or 26 of the first and second shoulder strap members 14, 16 are releasably attached to the intermediate portion of the base member 4. Such releasable attachment is preferably achieved by securing one component of a touch fastener, e.g. a hook touch fastener, on first inwardly facing surface of each of the second opposed ends 22, 26 and securing a much wider elongate strip of a second mating component of a touch fastener, e.g. a loop touch fastener, on an outwardly facing surface 44 of the intermediate portion of the base member 4. This will allow the secured position of the second opposed ends 22, 26 to be adjusted along the intermediate length of the base member 4, e.g. a few inches or so, to ensure that at least a portion of the second opposed ends 22, 26 is located rearwardly of the forward most portion of each shoulder of the wearer W to generate the resulting rearward and downward force F on each shoulder of the wearer W.

Since certain changes may be made in the above described shoulder support device, without departing from the spirit and scope of the invention herein involved, it is intended that all of the subject matter of the above description or shown in the accompanying drawings shall be interpreted merely as examples illustrating the inventive concept herein and shall not be construed as limiting the invention.

Wherefore, I claim:

1. A shoulder support device for facilitating correct posture of shoulders of a wearer, the shoulder support device comprising:

an elongate base member having first and second opposed free ends, each of the first and second opposed free ends having a mating attachment component to facilitate releasable attachment of the first and second opposed free ends with one another, and a spine support area being provided along an intermediate portion of the elongate base member for overlying a spine of the wearer; and a first shoulder strap member having first and second opposed ends and a second shoulder strap member having first and second opposed ends, the first end of each shoulder strap member being secured to the elongate base member adjacent the spine support area, and the second end of each of the shoulder strap members being secured to an intermediate portion of the elongate base member such that the second end of each of the shoulder strap members is located to communicate with an arm pit of the wearer, during use, without either the first or the second shoulder strap member overlapping one another or a spine of a wearer during use of the shoulder support device whereby each of the pair of spaced apart shoulder strap members exerts a resulting rearward and downward basing force on each shoulder of the wearer to influence each shoulder of the wearer into a correct posture position.

2. The shoulder support device according to claim 1, wherein the first end of each shoulder strap member is secured to the elongate base member adjacent one another but on opposed sides of the spine support area.

3. The shoulder support device according to claim 1, wherein the base member is both flexible and resilient to facilitate fitting snugly about a circumference of a chest portion of a wearer.

4. The shoulder support device according to claim 1, wherein the base member has a length typically between 24 and 50 inches.

5. The shoulder support device according to claim 4, wherein the base member has a length typically between 30 and 38 inches.

6. The shoulder support device according to claim 1, wherein the base member has a width typically between ½ to 4 inches.

7. The shoulder support device according to claim 1, wherein the base member has a width typically between about 1½ inches and 3½ inches.

8. The shoulder support device according to claim 1, wherein a first end of the first shoulder strap member is attached by stitching adjacent but spaced from the spine support area of the shoulder support device while a second opposed end of the first shoulder strap member is secured by stitching to an intermediate portion of the base member, and a first end of the second shoulder strap member is attached by stitching adjacent but spaced from an opposite side of the spine support area while a second opposed end of the second shoulder strap member is secured by stitching to an intermediate portion of the base member.

9. The shoulder support device according to claim 1, wherein the mating attachment components are one of a mating pair of hook and loop touch fasteners, a mating pair of snaps, and a mating pair of wire hooks and wire loops fasteners.

10. The shoulder support device according to claim 1, wherein each of the shoulder strap members supports a padding member to maximize comfort of the shoulder support device during use.

11. The shoulder support device according to claim 10, wherein each padding member which is adjustable along a length of the respective shoulder strap member.

12. The shoulder support device according to claim 10, wherein each padding member which is fixedly secured to the respective shoulder strap member.

13. The shoulder support device according to claim 1, wherein the communication between the second end of shoulder strap member and a respective arm pit of the wearer, during use, facilitates exerting a rearward biasing force on the respective shoulder forcing that respective shoulder of the wearer in a rearward direction during use.

14. The shoulder support device according to claim 1, wherein each of the shoulder strap members is under tension so as to exert a downward biasing force on the respective shoulder, pushing that respective shoulder in a downward direction.

15. The shoulder support device according to claim 1, wherein the communication between the second end of shoulder strap member and a respective arm pit of the wearer, during use, facilitates exerting a rearward biasing force on the respective shoulder forcing that respective shoulder in a rearward direction, and each of the shoulder strap members is under tension so as to exert a downward biasing force on the respective shoulder, pushing that respective shoulder in a downward direction, and the rearward biasing force and the downward biasing force combine with one another to form a combined resulting force on each shoulder.

16. The shoulder support device according to claim 14, wherein each padding members facilitate dissipating the resulting force, induced on the respective shoulders of the wearer, to allow the shoulder support device to be worn for prolonged periods of time without discomfort to the wearer.

17. A shoulder support device for facilitating correct posture of shoulders of a wearer, the shoulder support device comprising:

an elongate base member having first and second opposed free ends, each of the first and second opposed free ends having a mating attachment component to facilitate releasable attachment of the first and second opposed free ends with one another, and a spine support area being provided along an intermediate portion of the elongate base member for overlying a spine of the wearer;

a first shoulder strap member having first and second opposed ends and a second shoulder strap member having first and second opposed ends, the first end of each shoulder strap member being secured to the elongate base member adjacent the spine support area, and the second end of each of the shoulder strap members being secured to an intermediate portion of the elongate base member such that the second end of each of the shoulder strap members is located to communicate with an arm pit of the wearer, during use, without either the first or the second shoulder strap member overlapping one another or a spine of a wearer during use of the shoulder support device whereby each of the pair of spaced apart shoulder strap members exerts a resulting rearward and downward basing force on each shoulder of the wearer to influence each shoulder of the wearer into a correct posture position;

the first end of each shoulder strap member is secured to the elongate base member adjacent one another but on opposed sides of the spine support area to define the spine support area of a V-shaped configuration;

the base member has a width typically between about 1½ inches and 3½ inches; and each of the shoulder strap members supports a padding member to maximize comfort of the shoulder support device during use.

18. The shoulder support device according to claim 7, wherein the mating attachment components are one of a mating pair of hook and loop touch fasteners, a mating pair of snaps, and a mating pair of wire hooks and wire loops fasteners;

each padding member which is adjustable along the respective shoulder strap member; and the communication between the second end of shoulder strap member and a respective arm pit of the wearer, during use, facilitates exerting a rearward biasing force on the respective shoulder forcing that respective shoulder in a rearward direction, and each of the shoulder strap members is under tension so as to exert a downward biasing force on the respective shoulder, pushing that respective shoulder in a downward direction, and the rearward biasing force and the downward biasing force combine with one another to form a combined resulting force on each shoulder.

19. The shoulder support device according to claim 18, wherein each padding members facilitate dissipating the resulting force, induced on the respective shoulders of the wearer, to allow the shoulder support device to be worn for prolonged periods of time without discomfort to the wearer.

20. A method of supporting shoulders to facilitate correct posture of shoulders of a wearer, the method comprising the steps of:

providing an elongate base member having first and second opposed free ends, each of the first and second opposed free ends having a mating attachment component to facilitate releasable attachment of the first and second opposed free ends with one another, and a spine support area being provided along an intermediate portion of the elongate base member for overlying a spine of the wearer;

providing a first shoulder strap member having first and second opposed ends and a second shoulder strap member having first and second opposed ends, securing the first end of each shoulder strap member to the elongate base member adjacent the spine support area; and securing the second end of each of the shoulder strap members to an intermediate portion of the elongate base member such that the second end of each of the shoulder strap members is located to communicate with an arm pit of the wearer, during use, without either the first or the second shoulder strap member overlapping one another or a spine of a wearer during use of the shoulder support device to minimize pressure on a trapezius muscle of the wearer whereby each of the pair of spaced apart shoulder strap members exerts a resulting rearward and downward basing force on each shoulder of the wearer to influence each shoulder of the wearer into a correct posture position.

* * * * *